US009622655B2

(12) United States Patent
Sarver et al.

(10) Patent No.: US 9,622,655 B2
(45) Date of Patent: Apr. 18, 2017

(54) CORRECTION VALUES FOR IOL POWER ESTIMATES

(71) Applicant: WaveTec Vision Systems, Inc., Aliso Viejo, CA (US)

(72) Inventors: Edwin Jay Sarver, Carbondale, IL (US); Thomas D. Padrick, Seattle, WA (US)

(73) Assignee: WaveTec Vision Systems, Inc., Aliso Viejo, CA (US)

( * ) Notice: Subject to any disclaimer, the term of this patent is extended or adjusted under 35 U.S.C. 154(b) by 0 days.

(21) Appl. No.: 14/511,003

(22) Filed: Oct. 9, 2014

(65) Prior Publication Data

US 2015/0103313 A1   Apr. 16, 2015

Related U.S. Application Data

(60) Provisional application No. 61/889,477, filed on Oct. 10, 2013.

(51) Int. Cl.
*A61B 3/10* (2006.01)
*A61B 3/00* (2006.01)

(52) U.S. Cl.
CPC .......... *A61B 3/0025* (2013.01); *A61B 3/1005* (2013.01); *A61B 3/1015* (2013.01)

(58) Field of Classification Search
CPC ... A61B 3/0025; A61B 3/0058; A61B 3/1015; A61B 3/103; A61B 3/1173; A61B 3/1176; G02C 7/027; G02C 7/028; A61F 2/1637
USPC ....... 351/205, 246, 159.73, 159.74; 623/6.11
See application file for complete search history.

(56) References Cited

U.S. PATENT DOCUMENTS

| 6,736,510 B1 | 5/2004 | Van Heugten |
| 7,374,286 B2 | 5/2008 | Fujieda et al. |
| 7,556,378 B1 * | 7/2009 | Ianchulev ............ A61B 3/0033 351/205 |
| 7,883,505 B2 | 2/2011 | Van Heugten et al. |
| 8,480,659 B2 | 7/2013 | Frey et al. |
| 8,764,187 B2 | 7/2014 | Padrick et al. |
| 2003/0053025 A1 | 3/2003 | Turner et al. |

(Continued)

OTHER PUBLICATIONS

International Preliminary Report on Patentability, Application No. PCT/US2014/059943; 12 pages, Apr. 21, 2016.

(Continued)

*Primary Examiner* — Huy K Mai
(74) *Attorney, Agent, or Firm* — Baker Botts L.L.P.

(57) ABSTRACT

An ophthalmic method for determining relationships for calculating intraocular lens (IOL) power correction values is disclosed. The method may involve obtaining estimates of the postoperative optical power of a plurality of eyes undergoing IOL implant surgery. Measurements of the postoperative optical power and of one or more characteristics (e.g., axial length) of the eyes can also be obtained. The eyes can be separated into groups based upon their axial lengths. For each of the groups, a mathematical relationship can be determined for calculating IOL power correction values based on the measured characteristics. The mathematical relationship can reduce prediction error for the respective eyes in each group when applied to the corresponding estimates of the postoperative optical power. Methods and systems are also disclosed for using the IOL power correction values.

29 Claims, 3 Drawing Sheets

(56) References Cited

U.S. PATENT DOCUMENTS

| | | |
|---|---|---|
| 2011/0015541 A1 | 1/2011 | Padrick et al. |
| 2011/0242482 A1 | 10/2011 | Olsen |
| 2011/0270596 A1* | 11/2011 | Weeber ................... A61F 2/16 703/11 |
| 2013/0131687 A1 | 5/2013 | Ianchulev |

OTHER PUBLICATIONS

International Search Report and Written Opinion, Application No. PCT/US2014/059943; 16 pages, Jan. 14, 2015.
MA Nanavaty et al., "Anterior capsule cover and axial movement of intraocular lens," Eye (2008) 22, 1015-1023, 2008 Nature Publishing Group; 9 pages, 2008.

* cited by examiner

CORRECTION VALUES FOR IOL POWER ESTIMATES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application claims priority to U.S. Provisional Patent Application 61/889,477, filed Oct. 10, 2013 and entitled "CORRECTION FACTOR FOR IOL POWER ESTIMATES," which is hereby incorporated by reference herein in its entirety.

BACKGROUND

Field

The field of the invention relates to ophthalmic systems and procedures. In particular, the field of the invention relates to the determination and/or enhancement of intraocular lens (IOL) power values.

Description of the Related Art

Cataracts are clouded regions that can develop in the natural crystalline lens of an eye. A cataract can range in degree from slight clouding to complete opacity. Typically, formation of cataracts in human eyes is an age-related process. If left untreated, cataracts can lead to blindness. Surgeries have been developed for the treatment of cataracts by replacement of the natural crystalline lens with an artificial lens. Typically, an incision is made in the eye and the natural crystalline lens is removed. An artificial implant called an intraocular lens (IOL) is then inserted, for example, in the capsular bag of the eye in place of the natural crystalline lens. The spherical and/or astigmatic optical refractive power of the IOL may be selected so as to give the eye a desired amount of post-surgical refractive power. For example, the power of the IOL may be selected so as to place the eye in as close to an emmetropic state as possible when combined with the refractive power of the cornea of the eye.

SUMMARY

An ophthalmic method for determining relationships for calculating intraocular lens (IOL) power correction values is disclosed. In some embodiments, the method comprises: obtaining estimates of the postoperative optical power of a plurality of eyes undergoing IOL implant surgery; obtaining measurements of the postoperative optical power of the plurality of eyes; obtaining measurements of one or more characteristics of the plurality of eyes, the one or more characteristics comprising eye axial length; separating the plurality of eyes into a plurality of groups based upon their axial lengths; and for each of the plurality of groups, determining a mathematical relationship for calculating IOL power correction values based on the one or more characteristics, the mathematical relationship reducing prediction error for the respective plurality of eyes in each group when applied to the corresponding estimates of the postoperative optical power, the prediction error being based upon the respective differences between the estimates and measurements of the postoperative optical power for the plurality of eyes in each group.

An ophthalmic instrument is disclosed. In some embodiments, the ophthalmic instrument comprises: a measurement device for measuring the aphakic optical power of a patient's eye; and a processor for performing a method comprising, receiving an indication of the aphakic optical power of the patient's eye from the measurement device, determining an intraocular lens (IOL) power value based, at least in part, on the aphakic optical power of the patient's eye, receiving a measured axial length value for the patient's eye, selecting one of a plurality of possible relationships for calculating an IOL power correction value, the selected relationship being based upon the axial length value, determining, with the processor, an IOL power correction value, the IOL power correction value being determined from the selected relationship and from one or more characteristics of the patient's eye, and applying the IOL power correction value.

An ophthalmic method is disclosed. In some embodiments, the method comprises: receiving a measured axial length value for the eye of a patient; selecting one of a plurality of possible relationships for calculating an IOL power correction value, the selected relationship being based upon the axial length value; determining, with a processor, an IOL power correction value, the IOL power correction value being determined from the selected relationship and from one or more characteristics of the patient's eye; applying the IOL power correction value.

BRIEF DESCRIPTION OF THE DRAWINGS

For purposes of summarizing the disclosure, certain aspects, advantages and features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein. Certain embodiments are illustrated in the accompanying drawings, which are for illustrative purposes only.

DETAILED DESCRIPTION

Figure 1:
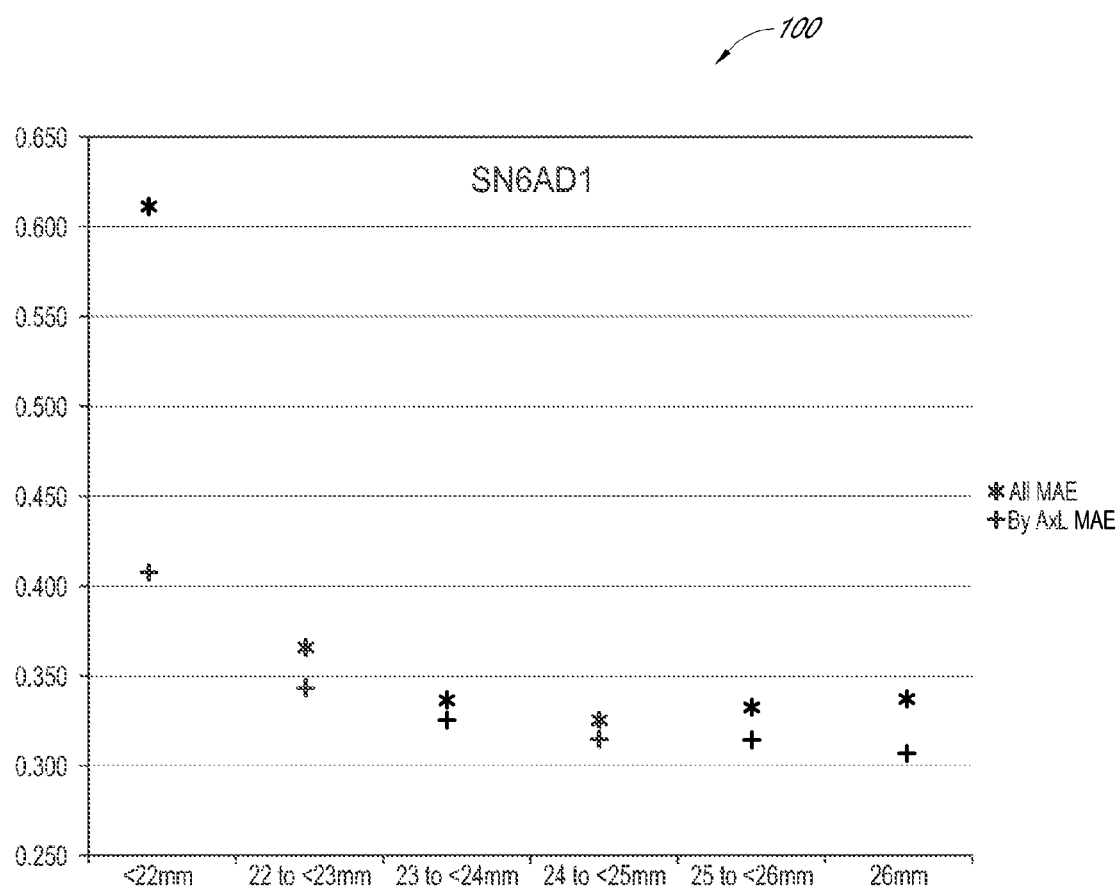
FIG. 1 is a graph that plots prediction error in intraocular lens (IOL) power estimates for a set of eyes as a function of the axial length of those eyes.

In a typical cataract surgery, a surgeon removes the natural crystalline lens from a patient's eye and an intraocular lens (IOL) is implanted in its place. By selecting an IOL having an appropriate amount of spherical and/or cylindrical power, an eye that prior to the surgery was, for example, myopic (near sighted), hyperopic (far sighted), and/or astigmatic can be brought to, for example, an emmetropic condition, or as close to an emmetropic condition as possible. The determination of an appropriate amount of IOL optical power for a given application is a significant aspect of obtaining satisfactory surgical outcomes for patients.

Various factors can be considered when calculating an estimate of the appropriate power for the IOL and/or when determining a correction value for an IOL power estimate, such as 1) the axial length of the eye, for example, measured from the cornea to the retina; 2) the total optical power of the cornea, including its anterior and posterior surfaces; 3) theoretical aphakic optical power (spherical and/or cylindrical); 4) white-to-white (WTW) distance; 5) the effective lens position (ELP) of the IOL, which can be understood, for example, as the distance from the corneal surface to the post-operative position of the IOL (e.g., the distance from corneal apex to the center of the IOL in its settled position); 6) a direct measurement of aphakic optical power (spherical and/or cylindrical) of the eye performed intraoperatively; and 7) the desired postoperative optical power (e.g., 0.0 diopters (D) of defocus for an emmetropic eye).

Preoperative biometry measurements can be used to measure the axial length of the eye, the curvature of the anterior surface of the cornea, and the white-to-white distance. The axial length of the eye can be measured, for example, by an ultrasound device or by Optical Coherence Tomography (OCT), while the curvature of the anterior surface of the cornea can be measured by, for example, a keratometer (e.g., K values measured in orthogonal meridians that pass through the corneal apex, or anatomical center, of the cornea and are expressed in terms of the radii of curvature or as the dioptric power of the cornea along these orthogonal meridians) or corneal topographer (simulated K values). The total optical power of the cornea can then be estimated from the corneal curvature K values. In addition, the aphakic ocular power of a patient's eye is dependent upon the total corneal power and the axial length of the patient's eye. In fact, theoretical aphakic ocular power values can be calculated from corneal power and axial length data.

The ELP of the IOL affects the total refractive power of the post-surgical eye because of the differing amount of vergence it imparts to light in the eye depending upon its spatial position between the cornea and the retina. For example, a 20 diopter IOL that is axially displaced from the predicted ELP by only 0.5 mm could result in a 1.0 diopter error in postoperative refraction. The ELP can be determined, for example, according to the methods described in U.S. Pat. No. 8,764,187, issued Jul. 1, 2014 and entitled "DETERMINATION OF THE EFFECTIVE LENS POSITION OF AN INTRAOCULAR LENS USING APHAKIC REFRACTIVE POWER," which is incorporated by reference herein in its entirety. Other methods can also be used for predicting the ELP.

In some embodiments, an intraoperative direct measurement of aphakic ocular power is made using a wavefront aberrometer (e.g., Talbot-Moiré, Shack-Hartmann, or others), though other instruments can also be used. The wavefront aberrometer may be mounted to, and optically aligned with, a surgical microscope used by the surgeon to perform the cataract surgery. Such a device is described in U.S. Pat. No. 7,883,505, issued Feb. 8, 2011 and entitled "INTEGRATED SURGICAL MICROSCOPE AND WAVEFRONT SENSOR," which is incorporated by reference herein in its entirety. One type of wavefront aberrometer that is suitable for performing the types of intra-operative measurements described herein is a Talbot-Moiré wavefront aberrometer such as the one described in U.S. Pat. No. 6,736,510, issued May 18, 2004 and entitled "OPHTHALMIC TALBOT-MOIRÉ WAVEFRONT SENSOR," which is incorporated by reference herein in its entirety.

Briefly, the Talbot-moiré wavefront aberrometer functions by introducing a probe laser beam into the patient's eye. The probe laser beam can be aligned to be coincident with the visual axis of the patient's eye, for example. The probe laser beam passes through the cornea, including the anterior and posterior surfaces, and is incident upon the retina. The probe beam scatters from the retina, for example, in such a way as to behave as a point source of light at the retina. The scattered probe beam light passes back through the eye, including the cornea. The optical wavefronts of the probe beam are altered according to the refractive properties of the eye (e.g., according to the shapes of the anterior and posterior surfaces of the cornea). The altered wavefront can then be analyzed to determine the optical power of the eye, including, for example, spherical power, astigmatic power, and astigmatic axis.

As the technology surrounding cataract surgeries continues to improve, increasingly, patients have expectations of being spectacle free after cataract surgery. In order to achieve emmetropic results for patients (or as close to emmetropic as possible), there is a need to improve IOL power estimates. Systems and methods are described herein, for estimating IOL power and/or improving estimates of IOL power for patients who are undergoing surgery to implant an IOL.

In some embodiments, a cataract surgery is performed by removing the natural crystalline lens from the patient's eye. In some embodiments, preoperative biometry measurements of, for example, axial length, corneal curvature (K), and/or white-to-white (WTW) distance can be made. The aphakic ocular power of the eye can be directly measured intraoperatively and/or theoretically calculated based on preoperative biometry measurements. ELP of the IOL can be estimated from a direct measurement of aphakic ocular power (e.g., spherical power, cylindrical power, spherical equivalent power, etc.) and/or from preoperative biometry measurements. An IOL power estimate can then be determined by processing electronics using a refractive IOL power formula that is a function of, for example, aphakic spherical equivalent (SE) power (SE=sphere value+½ the cylinder value) and of the ELP estimate. The IOL power formula may also be a function of K measurements.

In some embodiments, IOL power estimates can be calculated according to the following refractive vergence formula, where "Desired_PostRx" is the desired post-operative refraction and the "V" in each term is the vertex distance (e.g., 0 mm for "Aphakic_SE" and 13 mm for "Desired_PostRx"):

$$IOLPower = \frac{1336}{\frac{1336}{\frac{1000}{\text{Aphakic\_SE}} - V} + K} - ELP} - \frac{1336}{\frac{1336}{\frac{1000}{\text{Desired\_PostRx}} - V} + K} - ELP}$$

Other methods and formulas for determining IOL power estimates can also be used. Once the IOL power estimate has been determined, the surgeon can select an appropriate IOL, implant it in the eye (e.g., in the capsular bag), and complete the surgery.

An estimate of the postoperative optical power of the eye can be determined by, for example, solving the equation above for the Desired_PostRx as a function of IOL power. The estimate of the postoperative optical power of the eye can then be determined by evaluating the function for the particular power of the IOL selected for implantation. Post-surgery, actual measurements of the postoperative optical power of the eye can be performed in order to determine the amount of error in the estimates of postoperative optical power. Mathematical techniques, such as regression analysis, can then be used to identify mathematical relationships between various eye characteristics and the estimation error in order to improve results for future patients.

From a given set of data (e.g., >100 eyes per IOL model and/or per post refractive group) for which reliable postoperative manifest spherical equivalent (SE) optical power measurements can be obtained, the prediction error for estimating the postoperative SE optical power can be calculated. In some embodiments, the prediction error can be the mean absolute error between the estimated and measured postoperative optical power for the set of eyes. In other embodiments, the prediction error can be the percentage of the eyes having measured postoperative optical power that does or does not fall within a desired range (e.g., the percentage of eyes where postoperative SE is less than a selected threshold, such as +/−0.50 D).

A regression analysis using values for certain characteristics associated with the eyes and/or the implanted IOL can be performed to determine if there is a set of coefficients that, if applied to the values of such characteristics, can alter the estimated postoperative SE optical power estimates such that the overall prediction error for the data set is reduced or minimized. In some embodiments, a linear regression method can be used to minimize or reduce the prediction error and to generate the associated regression coefficients. However, higher-order regression and other techniques (e.g., neural networks, random trees, etc.) can also be used.

In some embodiments, the characteristics that are used in the regression analysis include the axial length, white-to-white (WTW) distance, directly-measured intraoperative aphakic optical power (e.g., aphakic SE), theoretically-calculated aphakic optical power (based on preoperative measurements), corneal curvature (e.g., average K), etc. In some embodiments, the regression analysis provides coefficients which, when multiplied by the respective values for these characteristics of a patient's eye and then summed together, result in a correction value which can be added to, for example, the estimate of the postoperative optical power for that patient's eye in order to reduce the error between predicted and measured postoperative optical power. The adjusted estimate of postoperative optical power can be used by a surgeon to determine which IOL power should be selected for the patient's eye. In some cases, the adjusted estimate of postoperative optical power may result in the surgeon selecting a different IOL power than he or she would have selected in the absence of the corrected estimate of postoperative optical power.

The inventors have observed that the prediction error for the estimates of postoperative optical power of the eyes varies depending on the axial length of the eyes. This is illustrated in FIG. 1, which is a graph 100 that plots prediction error in intraocular lens (IOL) power estimates for a set of eyes as a function of the axial length of those eyes. The data was obtained from a set of eyes which were implanted with a SN6AD1 model IOL. The set of eyes was divided into six groups based on the axial length of the eyes. In this case, the groups were divided at uniform axial length intervals. The first group includes all of those eyes having axial lengths less than 22 mm. The second group includes those eyes having axial lengths from 22 mm to less than 23 mm. The third group includes those eyes having axial lengths from 23 mm to less than 24 mm. The fourth group includes those eyes having axial lengths from 24 mm to less than 25 mm. The fifth group includes those eyes having axial lengths from 25 mm to less than 26 mm Finally, the sixth group includes those eyes having axial lengths greater than 26 mm.

When the prediction error for the six axial length groups is calculated using regression coefficients derived from the entire set of data, the results were poorer than when the prediction error for each of the six axial length groups is calculated separately using regression coefficients derived only from the eyes in each respective group. In the graph 100, asterisks (*) indicate the prediction error (in this case, the mean absolute error) for each group of eyes for the case where the regression analysis is performed using all of the eyes from all six groups. In contrast, plus signs (+) indicate the prediction error for each group of eyes for the case where the regression analysis is performed separately for each group using only eyes that are members of each respective group. As illustrated by the plot 100, the prediction error obtained by performing the regression analysis separately for each group was lower in each case than when the prediction error was obtained by performing the regression analysis on all of the eyes together without regard for the differing axial lengths of the eyes.

Thus, the segmented method of generating the regression coefficients is an improved method, especially for relatively short and long eyes. In some embodiments, a minimum of about 50 cases is used in each group in order to apply this segmented regression approach (though, in other embodiments more or fewer cases in each group could be used). To have 50 cases in the <22 mm axial length group generally would involve a relatively large set of data, as such eyes are relatively rare. Thus, it can be difficult to obtain the necessary data to perform this style of segmented regression analysis for each axial length bin.

As a result, rather than separating the eyes into groups at substantially uniform axial length intervals, the eyes can instead be separated into groups at non-uniform intervals which result in the groups having substantially uniform numbers of eyes in each group. This approach will be referred to as uniform grouping or clustering. In this approach one or more of the parameters used in the regression analysis is segregated into one or more relatively uniformly sized groups (versus the predefined axial length bins). In some embodiments, this approach allows for the benefits of the segmented analysis but without the restrictive element of needing a certain number of cases in each axial length bin, such as the less-than-22 mm bin. The groups which cover eye lengths which are more rare may encompass larger spans of axial length values than the groups which cover eye lengths which are more common. For example, a group can be formed of eyes having axial lengths that range from 20.5 mm to 23 mm which has the same number of data points as the other groups which may span shorter ranges of axial lengths.

As with the approach of segmenting at regular axial length intervals, regression can be used to generate coefficients for each group of eyes in the uniform clustering approach. In some embodiments, the minimum group or cluster size is about 50 data points. Further, in some embodiments, a maximum of about 20 groups can be formed (though fewer or more data points and fewer or more groups can also be used in some embodiments). In an embodiment that uses a minimum of 50 data points per group, for example, a total of two groups would be formed from a data set that includes 100 data points. Data sets with more than 1000 members could have 20 groups (assuming 50 data points per group). In some embodiments, the clustering rule could be the following: Number of Groups (N)=(Data Points)/50. In some embodiments, N could range from 2 to 20. A round down operation could be included so that a data set with, for example, 268 or 290 members would result in 5 groups (268/50=5.36→5 and 290/50=5.8→5). The foregoing is one example of how to formulate groups, though many other ways are also possible.

Figure 2:
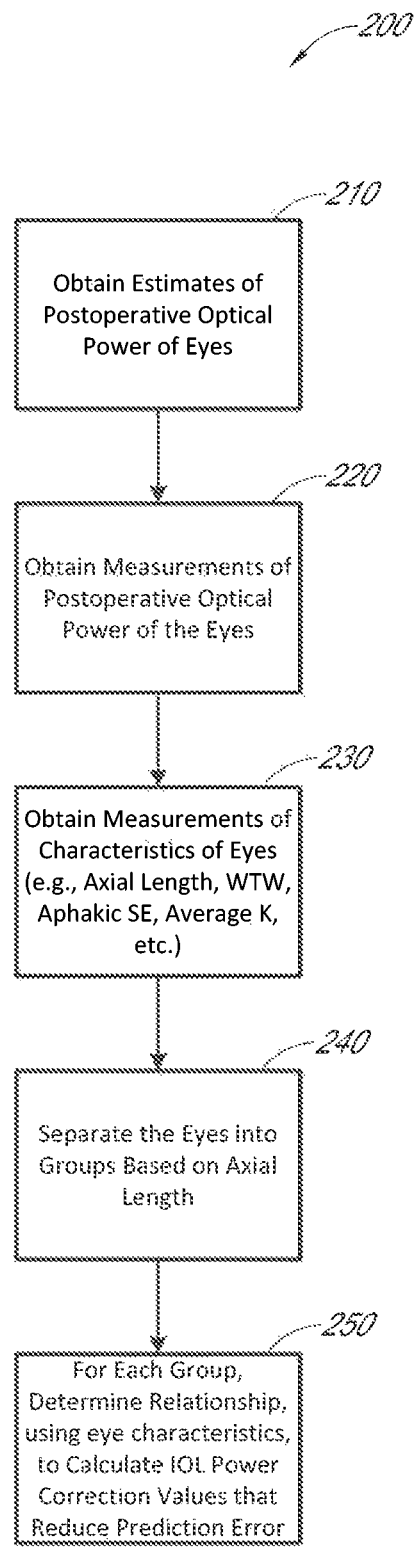
FIG. 2 is a flowchart that illustrates an embodiment of a method for determining relationships that can be used to calculate IOL power correction values that reduce error in IOL power estimates.

FIG. 2 is a flowchart that illustrates an embodiment of a method 200 for determining relationships that can be used to calculate IOL power correction values that reduce error in IOL power estimates. At block 210, estimates of the postoperative optical power for a set of eyes are obtained. In some embodiments, the eyes are ones that have all undergone IOL implantation surgery using the same commercially-available model of IOL. In some embodiments, the eyes are ones that have all previously undergone the same, or a similar, refractive surgery, such as LASIK or RK. An IOL power estimate can be determined for each eye prior to, or during, surgery. The IOL power estimate for each eye can be used as the basis for selecting the power of the IOL that is implanted into the eye. For the IOL power selected, the estimated postoperative optical power can be calculated using the refractive vergence formula, as discussed above. In some embodiments, the estimates of postoperative optical power are spherical equivalent power values, though other measures of optical power can also be used.

At block 220, actual measurements of the postoperative optical power of the eyes can be obtained. These measurements can be performed using, for example, an autorefractor, phoropter, or other suitable instrument. In some embodiments, the measurements of postoperative optical power are spherical equivalent power values, though other measures of optical power can also be used. These postoperative optical power measurements can be used to determine the error that was present in the estimates of the postoperative optical power. In some embodiments, an error value is determined for each eye in the data set, and a prediction error value can be determined for the data set as a whole, or for sub-portions of the data set, as discussed further herein. In some embodiments, the prediction error value is the average absolute error for the eyes in the data set. In some embodiments, the prediction error value is the median absolute error for the eyes in the data set. In other embodiments, the prediction error value is the percentage of eyes where the postoperative optical power is outside of a desired range (e.g., the percentage of eyes which do not achieve less than +/−0.50 D of postsurgical SE optical power).

At block 230, measurements of various characteristics of the eyes in the data set can be obtained. As discussed herein, these characteristics can include, for example, axial length. WTW distance, aphakic SE power (whether directly measured intraoperatively or theoretically calculated based on preoperative measurements), average corneal curvature, etc. In some embodiments, one of the characteristics is a composite of two or more other characteristics. For example, the delta aphakic optical power, which can be defined as theoretical aphakic SE−measured aphakic SE, is used. The inventors have found that this delta aphakic optical power value can advantageously be more strongly correlated with prediction error than either the theoretical aphakic power value or the measured aphakic power value alone.

At block 240, the eyes in the data set can be separated into groups based on their axial length values. As discussed herein, the separation can be done by forming groups at regular axial length intervals, such that the groups span substantially uniform ranges of axial lengths. Alternatively, the separation can be done by forming groups that span non-uniform ranges of axial lengths but include substantially uniform numbers of eyes. An example algorithm for performing this type of uniform clustering is now presented.

The goal of this uniform clustering algorithm is to divide up an R-dimensional set of data into groups of approximately equal members. As a simple example, suppose we have a 1-dimensional set of 10 values and we want to divide it into two equal partitions. (Note multiple values are allowed.)

| 20 |
|----|
| 2  |
| 10 |
| 8  |
| 19 |
| 18 |
| 19 |
| 17 |
| 15 |
| 11 |

First, the data can be sorted. Then, the data can be split into two groups, A and B, each of size 5=10/2=(number of values)/(number of partitions).

| 2  | A |
|----|---|
| 8  | A |
| 10 | A |
| 11 | A |
| 15 | A |
| 17 | B |
| 18 | B |
| 19 | B |
| 19 | B |
| 20 | B |

Define the following: N=number of values, integer, M=number of partitions, integer. Now, the following integer valued region separator indices s(m) for m=0 to M−1 can be computed.

$$s(m) = \text{Round}\left(m \times \frac{N}{M}\right)$$

If the sorted data is called x[n] for n=0 to N−1, then the real valued region separator values c(m) for m=0 to M−1 are given by:

$$c(m) = x[s(m)]$$

For the example data above, c[0]=2 and c[1]=17. We use the m index (m=0 to M−1) to label the regions. Given a value z, the index label of the corresponding region can be computed using the following equation.

$$m = \begin{cases} 0 & \text{for } z < c[1] \\ M-1 & \text{for } c[M-1] \leq z \\ k & \text{for } c[k] \leq z < c[k+1] \end{cases}$$

As a second example using the original data, suppose now M=3. The region separator indices are:

$$s(0) = \text{Round}(0) = 0$$

$$s(1) = \text{Round}(10/3) = \text{Round}(3.333) = 3$$

$$s(2) = \text{Round}(2*10/3) = \text{Round}(6.666) = 7$$

The region separator values are:

$$c(0)=x[0]=2$$

$$c(1)=x[3]=11$$

$$c(2)=x[7]=19$$

A few given values of z and the corresponding index labels are:

| z | m |
|---|---|
| −1 | −0 |
| 1 | 0 |
| 10 | 0 |
| 11 | 1 |
| 18 | 1 |
| 19 | 2 |
| 20 | 2 |
| 22 | 2 |

To extend this clustering concept to higher dimensions, we select the number of intervals per dimension, M[j], j=0 to J−1 where J is the number of dimensions. The foregoing equations can then be applied for each dimension. Note that there is no requirement for M[i]=M[j] for i≠j.

To use this clustering in the context of IOL power estimates and correction values, the input data can be grouped according to the clustering schemes above (e.g., based upon the axial lengths of the eyes in the data set). Then, a linear predictor can be applied to each group of data, as discussed further herein. The foregoing equation for calculating index labels can be applied to each dimension to give the J-dimensional index of the linear predictor to use during IOL outcome prediction.

At block 250 of FIG. 2, a relationship can be determined for calculating IOL power correction values that reduce prediction error for the eyes in each respective group that is determined at block 240. As already mentioned, in some embodiments, this can be done using regression analysis. The regression analysis can be performed separately on each axial length group of eyes in the data set. The regression analysis can be used to model the mathematical relationship between the various eye characteristics discussed herein (and/or characteristics of the IOL that was implanted in those eyes) and the prediction error for the selected axial length group of eyes, or a parameter directly associated with the production error.

The regression analysis can be used to improve or optimize a target parameter. The target parameter may be the prediction error associated with a selected axial length group of eyes, or another parameter directly associated with the prediction error. For example, the eye characteristics can be regressed against the known prediction error to obtain, for example, a 0.00 mean prediction error for the eyes in the selected axial length bin. This results in a set of coefficients that, when used to correct the IOL power estimates for the eyes in the selected axial length group, results in 0.00 mean prediction error for that group of eyes. These coefficients can be used to correct IOL power estimates for future patients by applying the coefficients that correspond to the axial length group to which the eyes of those future patients belong. In another example, the eye characteristics can be regressed against the prediction error to increase or maximize the percentage of eyes in the selected axial length group whose postoperative optical power is less than a desired threshold (e.g., less than +/−0.50 D).

In some embodiments, the data corresponding to each and every eye in the axial length group are factored into the resulting regression coefficients. For example, if a particular axial length group of eyes included sets of data for 500 eyes, the regression analysis can determine the regression coefficients using all 500 data points in an attempt to minimize or reduce the prediction error. In other embodiments, however, it can be advantageous to use only the data corresponding to a subset of representative eyes in each axial length group. This can be done using, for example, a random sample consensus (RANSAC) algorithm.

RANSAC is a computational algorithm that attempts to estimate one or more parameters of a mathematical model from a set of observed data. The algorithm is designed to tolerate a relatively large fraction of outlier data that should be ignored while it fits the remainder of good data in a training set. The RANSAC algorithm assumes that the data in each axial length group consists of inliers whose distribution can be relatively well accounted for by the relationship between the chosen eye characteristics and the prediction error. The RANSAC algorithm also assumes, however, that the data in each axial length group consists of outliers which do not fit the model. In the application of optimizing intraocular lens (IOL) case histories to improve prediction of postoperative refraction error, the outlier data could be due to data that was not correctly recorded, biometric measurement errors, or very unusual optical results due to unknown reasons. The RANSAC algorithm can determine the regression coefficients primarily based on the inliers rather than the outliers. Through empirical evaluation of several large IOL data sets, algorithm parameters, error measures, and termination criteria can be established that lead to robust and efficient estimates.

The RANSAC algorithm does not use all of the data to determine the regression coefficients. Instead, the algorithm can randomly select a subset of the eyes in each axial length group. In some embodiments, the number of selected eyes can be a multiple of the number of eye characteristics that are being considered in the regression analysis. For example, if the regression analysis were to consider four eye characteristics (e.g., axial length, WTW distance, delta aphakic optical power, and average K), then the number of randomly selected eyes could be a multiple of four. In some embodiments, the algorithm randomly selects a number of eyes corresponding to two times the number of eye characteristics being considered. Thus, for an axial length group that includes 500 cases, the algorithm randomly selects only eight sets of data to analyze at a time (though other numbers of eyes/data sets can be used).

The algorithm then performs a linear regression analysis to identify a set of coefficients that improve or optimize the prediction error for the selected subset of eyes. These regression coefficients are then applied to the entire axial length group and the resulting prediction error is determined. The algorithm then randomly selects a new set of eight eyes from the axial length group and a new set of coefficients are calculated and then applied to the entire axial length group of eyes. If the new set of coefficients results in better prediction error than the coefficients calculated from the first set of randomly-selected eyes, then the first set of coefficients is disregarded. This process repeats iteratively (e.g., tens of thousands of times) until the resulting prediction error is satisfactorily improved or optimized.

By not using all of the data to calculate the regression coefficients for each axial length group, the algorithm effectively eliminates bad or extreme data which would "pull" the coefficients away from a more optimal solution. While this data (bad or extreme) is not used in the RANSAC regression analysis, it is used in calculating the resulting prediction error (mean average error) for the axial length group. All of the data can also be used in calculating statistical metrics such as the standard deviation and median. Thus, the algorithm does not filter out the "bad" data points but rather simply does not use them in the regression. Instead, the regression coefficients for each axial length group are based on the particular subset of randomly selected eyes within that group which result in an improved or optimized prediction error for the entire group.

Once again, the algorithm is not required to improve or optimize only a single measure of prediction error, such as mean average error. Instead, it can be used to improve or optimize any desired measure of prediction error. For example, surgeons may have difficulty in understanding that a mean average error of 0.33+/−0.25 is much better than a mean average error of 0.38+/−0.32. But they do appreciate postoperative SE of 85% of eyes being less than +/−0.50 D versus only 75%. Thus, the regression algorithm can improve or optimize the percentage of eyes in each axial length group having postoperative SE<+/−0.50 D. The regression analysis results in a data curve which is not the typical bell shaped distribution but one that is a relatively fatter at the top and narrower at the base with a similar mean. The algorithm forces more data into the "sweet spot" of less than +/−0.5 D prediction error by finding data sets within the axial length group which improved or optimize this target.

If a data set includes 20 axial length groups with 50 eyes each (1000 total eyes) and the regression coefficients for each group are calculated from only eight of the 50 eyes, then the foregoing technique would result in 20 sets of regression coefficients generated from 160 of the 1000 eyes. As there are different sets of regression coefficients for each axial length group, discontinuities will likely exist between the coefficients of neighboring axial length groups. In some embodiments, it may be advantageous to avoid such discontinuities between axial length groups. For example it may be desirable that a calculated IOL, power correction value for an eye having an axial length of 23.99 mm would be substantially similar to the correction value for an eye having an axial length of 24.01 mm. In order to accomplish this aim, blend zones can be defined between each pair of neighboring axial length groups and blend zone coefficients can be determined for each such blend zone.

The blend zone may consist of, for example, ⅛ of the width of each axial length group at its borders (though other fractions of the width of an axial length group could also be used). Thus, if the axial length of an eye for which an IOL power correction value is to be calculated falls somewhere in the central ⅝ of an axial length group, then the regression coefficients corresponding to that group would be applied. If, however, the new data point lies within ⅛ of a border between two axial length groups, then the regression coefficients corresponding to the blend zone would be used for that data point. The ⅛ value could be a variable that ranges from ½ to ⅛ depending on the number of data points in the set at the time of optimization. Other fractions can also be used. To determine the regression coefficients for each blend zone, a linear blend of the regression coefficients from the two neighboring clusters may be calculated. Other methods of blending the regression coefficients from neighboring axial length groups can also be used. If blend zone coefficients are implemented, this will result in an additional N−2 sets of regression coefficients, where N is equal to the total number of axial length groups. Thus, in such embodiments, the total number of sets of regression coefficients will be 2N−2.

Figure 3:
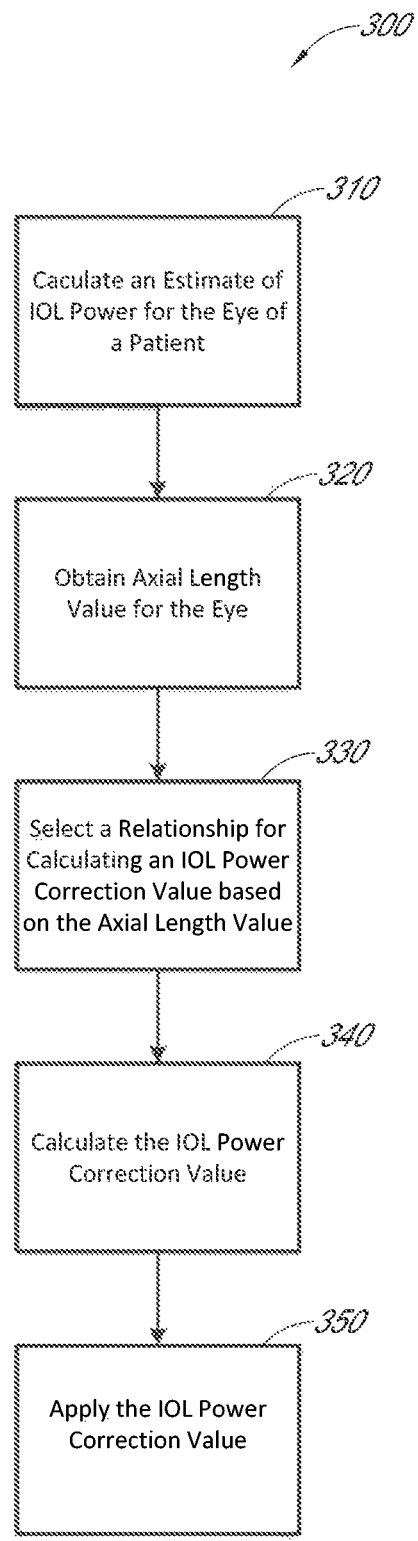
FIG. 3 is a flowchart that illustrates an embodiment of a method for enhancing an estimate of the optical power of an intraocular lens (IOL) to be inserted into the eye of a patient.

FIG. 3 is a flowchart that illustrates an embodiment of a method 300 for enhancing an estimate of the optical power of an intraocular lens (IOL) to be inserted into the eye of a patient. At block 310, an estimate of the IOL power for the eye of a patient is calculated. In some embodiments, the IOL power estimate is calculated based, at least in part, on an aphakic optical power value for the patient's eye. The aphakic optical power value can be measured intraoperatively using a wavefront aberrometer, as discussed herein. The wavefront aberrometer can be integrated with a surgical microscope, as discussed herein. The IOL power estimate can be calculated using, for example, the refractive convergence formula set forth herein. Other techniques can also be used, however.

At block 320, an axial length value for the eye of the patient is obtained. The axial length value can be measured using any conventional technique.

At block 330, a processor selects a relationship for calculating an IOL power correction value based on the axial length value of the patient's eye. As discussed herein, regression coefficients are targeted for each of a plurality of axial length groups. The processor may determine which of the axial length groups the patient's eye belongs to and the regression coefficients corresponding to that axial length group can be selected.

At block 340, the processor calculates the IOL power correction value. This can be done by, for example, multiplying each of the respective regression coefficients times the value of a corresponding characteristic of the patient's eye. As discussed herein, such characteristics can include the axial length, the WTW distance, the theoretical aphakic optical power, the measured aphakic optical power, the difference between the theoretical aphakic optical power and the measured aphakic optical power, and the average corneal curvature. In some embodiments, the IOL power correction value is calculated as A*(axial length)+B*(WTW distance)+C*(theoretical aphakic optical power−measured aphakic optical power)+D*(average corneal curvature), where A, B, C, and D represent the regression coefficients corresponding to the axial length group to which the patient's eye belongs.

Finally, at block 350, the IOL power correction value is applied. For example, in some embodiments, the IOL power correction value is applied to an estimate of postoperative optical power of the patient's eye for a given IOL power value. In some embodiments, this is done by simply adding the IOL power correction value to the estimate of postoperative optical power. However, in other embodiments, the IOL power correction value may be applied according to some other mathematical relationship with the estimate of postoperative optical power. The resulting adjusted estimate of postoperative optical power can provide a surgeon with a more accurate representation of what the postoperative optical power of a patient will be for a given IOL power value. As a result, the surgeon can more accurately select the power of the IOL to be implanted into the patient's eye.

The foregoing embodiments have been described at a level of detail to allow one of ordinary skill in the art to make and use the devices, systems, methods, etc. described herein. A wide variety of variation is possible, however. For example, components, elements, and/or steps may be altered, added, removed, or rearranged.

The systems and methods described herein can advantageously be implemented using, for example, computer software, hardware, firmware, or any combination of software, hardware, and firmware. Software modules can comprise computer executable code for performing the functions described herein. In some embodiments, computer-executable code is executed by one or more general purpose computers. However, a person of ordinary skill in the art will appreciate, in light of this disclosure, that any module that can be implemented using software to be executed on a general purpose computer can also be implemented using a different combination of hardware, software, or firmware. For example, such a module can be implemented completely in hardware using a combination of integrated circuits. Alternatively or additionally, such a module can be implemented completely or partially using specialized computers designed to perform the particular functions described herein rather than by general purpose computers. In addition, where methods are described that are, or could be, at least in part carried out by computer software, it should be understood that such methods can be provided on computer-readable media (e.g., optical disks such as CDs or DVDs, hard disk drives, flash memories, diskettes, or the like) that, when read by a computer or other processing device, cause it to carry out the method.

A person of ordinary skill in the art will also appreciate, in light of this disclosure, that multiple distributed computing devices can be substituted for any one computing device illustrated herein. In such distributed embodiments, the functions of the one computing device are distributed such that some functions are performed on each of the distributed computing devices.

While certain embodiments have been explicitly described, other embodiments will become apparent to those of ordinary skill in the art based on this disclosure. Therefore, the scope of the invention is intended to be defined by reference to the claims and not simply with regard to the explicitly described embodiments.

What is claimed is:

1. An ophthalmic method for determining relationships for calculating intraocular lens (IOL) power correction values, the method comprising:
    obtaining estimates of a postoperative optical power of a plurality of eyes that have not undergone an IOL implant surgery;
    obtaining measurements of the postoperative optical power of the plurality of eyes after the IOL implant surgery;
    obtaining measurements of one or more characteristics of the plurality of eyes, the one or more characteristics comprising an eye axial length;
    separating the plurality of eyes into a plurality of groups based upon the axial eye lengths; and
    for each of the plurality of groups, determining a mathematical relationship for calculating IOL power correction values based on the one or more characteristics, the mathematical relationship reducing a prediction error value for the respective plurality of eyes in each group when applied to the corresponding estimates of the postoperative optical power, the prediction error value being based upon the respective differences between the estimates and measurements of the postoperative optical power for the plurality of eyes in each group.

2. The ophthalmic method of claim 1, wherein the same commercially-available IOL product is implanted into each of the plurality of eyes.

3. The ophthalmic method of claim 1, wherein each of the plurality of eyes has undergone a previous refractive surgery.

4. The ophthalmic method of claim 1, wherein the prediction error value comprises the average error for the estimates of the postoperative optical power, or wherein the prediction error value comprises the percentage of the plurality of eyes for which the postoperative optical power is outside a predetermined range.

5. The ophthalmic method of claim 1, wherein the plurality of eyes are separated into a plurality of groups at substantially equal axial length intervals.

6. The ophthalmic method of claim 1, wherein the plurality of eyes are separated into a plurality of groups having substantially equal numbers of eyes in each group.

7. The ophthalmic method of claim 6, wherein the minimum number of eyes in each group is about 50.

8. The ophthalmic method of claim 1, wherein the mathematical relationship is determined using only a subset of the plurality of eyes in each of the plurality of groups.

9. The ophthalmic method of claim 8, wherein the subset of the eyes is randomly selected.

10. The ophthalmic method of claim 1, wherein the mathematical relationship is determined using a random sample consensus (RANSAC) algorithm.

11. The ophthalmic method of claim 1, wherein determining a mathematical relationship for calculating IOL power correction values comprises determining a coefficient for each of the one or more characteristics.

12. The ophthalmic method of claim 11, wherein the coefficients are determined using regression.

13. The ophthalmic method of claim 11, further comprising determining blended coefficients for use in blend zones adjacent boundaries between the plurality of groups, the blended coefficients comprising a combination of the coefficients corresponding to the groups on either side of each boundary.

14. The ophthalmic method of claim 1, wherein the one or more characteristics of the plurality of eyes further comprise at least one of: a measured aphakic optical power, a theoretical aphakic optical power, a corneal power, and a white-to-white distance.

15. The ophthalmic method of claim 14, wherein the one or more characteristics further comprise a difference between the theoretical aphakic optical power and the measured aphakic optical power.

16. An ophthalmic instrument comprising:
    a measurement device for measuring the aphakic optical power of a patient's eye; and
    a processor having access to memory media storing instructions executable by the processor for,
        receiving an indication of the aphakic optical power of the patient's eye from the measurement device,
        determining an intraocular lens (IOL) power value based, at least in part, on the aphakic optical power of the patient's eye,
        receiving a measured axial length value for the patient's eye,
        selecting a mathematical relationship for calculating an IOL power correction value, wherein the mathematical relationship is based upon the axial length value and reduces a prediction error of the IOL power correction value for a group of eyes having similar axial length values as the axial length value,
        determining an IOL power correction value based on the mathematical relationship and one or more characteristics of the patient's eye, and
        selecting an IOL for the patient's eye based on the IOL power correction value.

17. The ophthalmic instrument of claim 16, wherein the measurement device comprises a wavefront aberrometer and the aphakic optical power comprises a direct measurement of aphakic optical power.

18. The ophthalmic instrument of to claim 17, wherein the wavefront aberrometer comprises a Talbot-moiré wavefront aberrometer.

19. The ophthalmic instrument of claim 16, wherein the one or more characteristics of the patient's eye comprise at least one of: an axial length, a measured aphakic optical power, a theoretical aphakic optical power, a corneal power, and a white-to-white distance.

20. The ophthalmic instrument of claim 19, wherein one of the one or more characteristics comprises a difference between the theoretical aphakic optical power and the measured aphakic optical power.

21. The ophthalmic instrument of claim 16, wherein determining the IOL power correction value further comprises identifying one or more coefficients, each of the coefficients corresponding to one of the one or more characteristics of the patient's eye.

22. The ophthalmic instrument of claim 16, wherein selecting the IOL for the patient's eye further comprises:
applying the IOL power correction value to an estimate of a postoperative optical power of the patient's eye.

23. An ophthalmic method comprising:
receiving a measured axial length value for the eye of a patient;
selecting a mathematical relationship for calculating an IOL power correction value, wherein the mathematical relationship is based upon the axial length value and reduces a prediction error of the IOL power correction value for a group of eyes having similar axial length values as the axial length value;
determining, with a processor, the IOL power correction value based on the mathematical relationship and one or more characteristics of the patient's eye; and
selecting an IOL for the patient's eye based on the IOL power correction value.

24. The ophthalmic method of claim 23, wherein the one or more characteristics of the patient's eye comprise at least one of: an axial length, a measured aphakic optical power, a theoretical aphakic optical power, a corneal power, and a white-to-white distance.

25. The ophthalmic method of claim 24, wherein one of the one or more characteristics comprises a difference between the theoretical aphakic optical power and the measured aphakic optical power.

26. The ophthalmic method of claim 23, wherein determining the IOL power correction value further comprises identifying one or more coefficients, each of the coefficients corresponding to one of the one or more characteristics of the patient's eye.

27. The ophthalmic method of claim 23, wherein selecting the IOL for the patient's eye further comprises:
applying the IOL power correction value to an estimate of a postoperative optical power of the patient's eye.

28. The ophthalmic method of claim 27, wherein applying the IOL power correction value comprises adding the IOL power correction value to the estimate of the postoperative optical power of the patient's eye.

29. The ophthalmic method of claim 23, wherein the IOL power correction value is determined using a refractive vergence formula.

* * * * *